United States Patent [19]

Le et al.

[11] Patent Number: 5,545,180
[45] Date of Patent: Aug. 13, 1996

[54] UMBRELLA-SHAPED SUTURE ANCHOR DEVICE WITH ACTUATING RING MEMBER

[75] Inventors: Thu A. Le, Matawan; Sung S. Yi, Princeton; William Zwaskis, Fanwood; Jack S. Pedlick, Butler; Brian H. Luscombe, Warren; Dennis D. Jamiolkowski, Long Valley; John Di Giovanni, Woodbridge; Keith A. Seritella, South Brunswick, all of N.J.; Mark G. Steckel, Mainville, Ohio; Steven F. Harwin, New York, N.Y.

[73] Assignee: Ethicon, Inc., New Brunswick, N.J.

[21] Appl. No.: 235,024

[22] Filed: Apr. 28, 1994

Related U.S. Application Data

[63] Continuation-in-part of Ser. No. 166,493, Dec. 13, 1993.

[51] Int. Cl.⁶ ................................................. A61B 17/04
[52] U.S. Cl. ........................... 606/232; 606/73; 606/75
[58] Field of Search ................................. 606/72, 74, 75, 606/220, 232; 411/340, 508, 509, 510, 511, 904

[56] References Cited

U.S. PATENT DOCUMENTS

| | | |
|---|---|---|
| D. 331,463 | 12/1992 | Rosenberg et al. . |
| D. 331,626 | 12/1992 | Hayhurst et al. . |
| 4,011,602 | 3/1977 | Rybichie et al. . |
| 4,013,071 | 3/1977 | Rosenberg . |
| 4,632,100 | 12/1986 | Somers et al. . |
| 4,721,103 | 1/1988 | Freedland . |
| 4,738,255 | 4/1988 | Goble et al. ........................... 606/232 |
| 4,759,765 | 7/1988 | Van Kampen . |
| 4,772,286 | 9/1988 | Goble et al. . |
| 4,784,126 | 11/1988 | Hourahane . |
| 4,828,562 | 5/1989 | Kenna . |
| 4,834,752 | 5/1989 | Van Kempen . |
| 4,851,005 | 7/1989 | Hunt et al. . |
| 4,870,957 | 10/1989 | Goble et al. . |
| 4,895,148 | 1/1990 | Bays et al. . |
| 4,898,156 | 2/1990 | Gatturna et al. . |
| 4,924,865 | 5/1990 | Bays et al. . |
| 4,927,421 | 5/1989 | Goble . |
| 4,976,715 | 12/1990 | Bays et al. . |
| 5,002,550 | 3/1991 | Li . |
| 5,013,316 | 5/1991 | Goble . |

(List continued on next page.)

FOREIGN PATENT DOCUMENTS

| | | |
|---|---|---|
| 0464479 | 1/1992 | European Pat. Off. . |
| 0464480 | 1/1992 | European Pat. Off. . |
| 0502509 | 9/1992 | European Pat. Off. . |
| 0504915 | 9/1992 | European Pat. Off. . |
| WO8603666 | 7/1986 | WIPO . |
| WO8809157 | 12/1988 | WIPO . |

OTHER PUBLICATIONS

Patent Search Abstracts, US 4,409,974, (Oct. 18, 1985), all from the WPAT database on Orbit by Charles G. Fritz, Nov. 25, 1992.
Patent Search Abstracts, US 4,537,185 (Aug. 27, 1985).
Patent Search Abstracts, US 4,632,100 (Dec. 30, 1986).
Patent Search Abstracts, AU 918 7367 (Apr. 15, 1992), all for the WPAT database on Orbit by Charles G. Fritz, Nov. 25, 1992.
Patent Search Abstracts, EP 502 509, (Sep. 9, 1992).
Patent Search Abstracts, EP 502 698 (Sep. 9, 1992).
Patent Search Abstracts, US 4,632,100 (Dec. 30, 1986).
Patent Search Abstracts, US 4,738,255 (Apr. 19, 1988).

(List continued on next page.)

*Primary Examiner*—Gary Jackson
*Attorney, Agent, or Firm*—Rosenman & Colin

[57] ABSTRACT

A suture anchor device having an anchor member with outwardly extending wing members and an actuating wedge member. The suture anchor device is inserted into a bore hole in a bone as part of an orthopedic surgical procedure wherein soft tissue such as a tendon or ligament is attached to the surface of the bone. The wing members are spread outwardly by the wedge member to lock the suture anchor device in the bone. The suture anchor has similar utility in soft tissue applications.

26 Claims, 11 Drawing Sheets

U.S. PATENT DOCUMENTS

| | | | |
|---|---|---|---|
| 5,037,422 | 8/1991 | Hayhurst | 606/232 |
| 5,041,129 | 8/1991 | Hayhurst et al. | 606/232 |
| 5,064,425 | 11/1991 | Branemark et al. | 606/72 |
| 5,084,050 | 1/1992 | Draenert | 606/77 |
| 5,100,417 | 3/1992 | Cerier et al. | 606/232 |
| 5,102,414 | 4/1992 | Kirsch | 606/73 |
| 5,116,337 | 5/1992 | Johnson . | |
| 5,129,906 | 7/1992 | Ross et al. . | |
| 5,141,520 | 8/1992 | Goble et al. | 606/232 |
| 5,147,362 | 9/1992 | Goble . | |
| 5,152,790 | 10/1992 | Rosenberg et al. . | |
| 5,167,665 | 12/1992 | McKinney . | |
| 5,176,682 | 1/1993 | Chow . | |
| 5,192,303 | 3/1993 | Gatturna et al. . | |
| 5,203,784 | 4/1993 | Ross et al. | 606/104 |
| 5,224,946 | 7/1993 | Hayhurst et al. | 606/232 |
| 5,236,445 | 8/1993 | Hayhurst et al. | 606/232 |
| 5,258,016 | 11/1993 | DiPoto et al. | 606/232 |
| 5,268,001 | 12/1993 | Nicholson et al. | 606/72 |
| 5,354,298 | 10/1994 | Lee et al. | 606/72 |
| 5,383,905 | 1/1995 | Golds et al. | 606/232 |

OTHER PUBLICATIONS

Patent Search Abstracts, US 4,741,330 (May 3, 1988).
Patent Search Abstracts. US 4,744,353 (May 17, 1988).
Patent Search Abstracts, US 4,899,743 (Feb. 13, 1990).
Patent Search Abstracts, US 4,946,468 (Aug. 7, 1990).
Patent Search Abstracts, US 4,968,315 (Nov. 6, 1990).
Patent Search Abstracts, US 4,988,351 (Jan. 29, 1991).
Patent Search Abstracts, US 5,046,513 (Sep. 10, 1991).
Patent Search Abstracts, US 5,100,417 (Mar. 31, 1992).
Patent Search Abstracts, US 5,139,520 (Aug. 18, 1992).
Patent Search Abstracts, US 5,141,520 (Aug. 25, 1992).

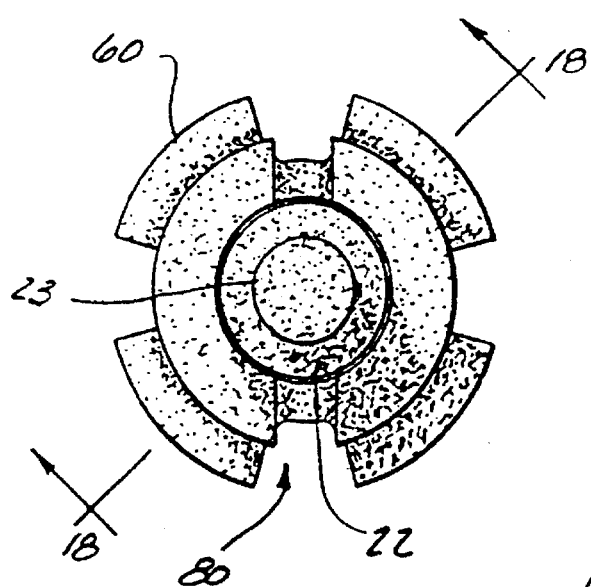
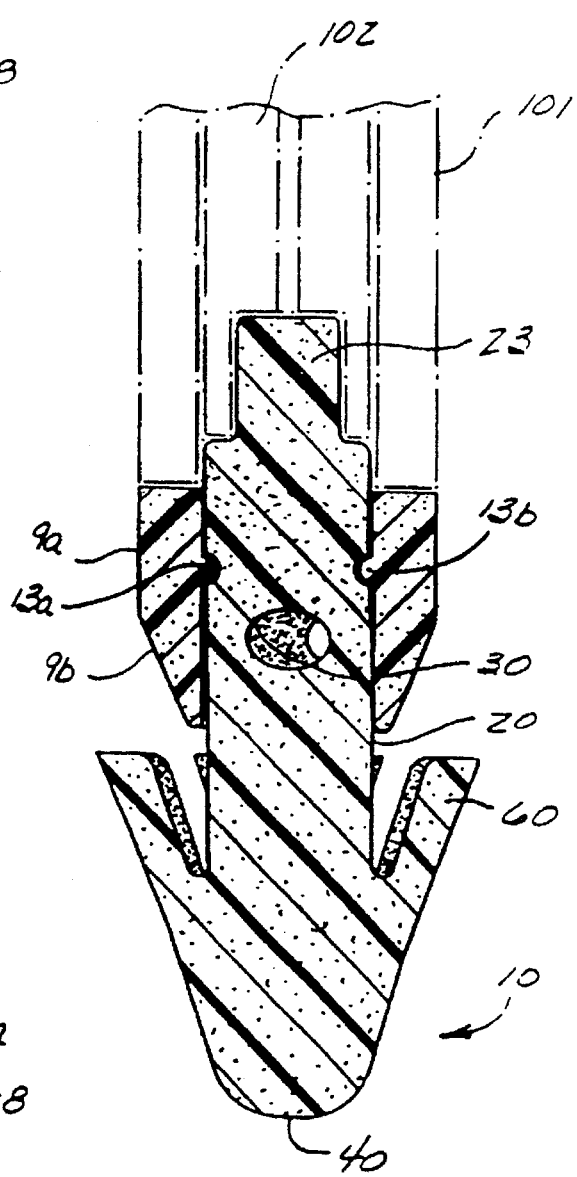
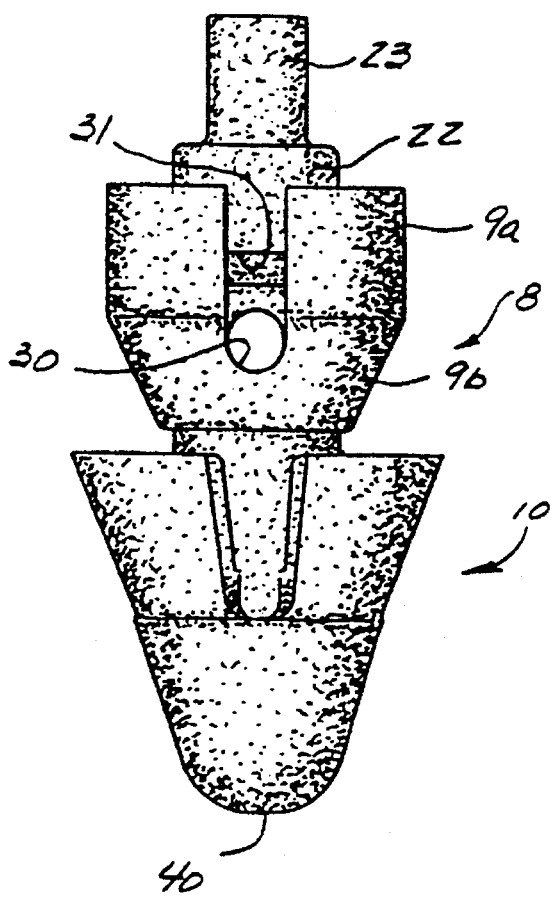

UMBRELLA-SHAPED SUTURE ANCHOR DEVICE WITH ACTUATING RING MEMBER

CROSS-REFERENCE

This is a continuation-in-part of application Ser. No. 08/166,493, filed Dec. 13, 1993, the contents of which are incorporated herein by reference thereto.

TECHNICAL FIELD

The field of art to which this invention relates is suture anchors, more specifically, to suture anchors for attaching soft tissue to bone.

BACKGROUND ART

As the treatment of injuries to joints and soft tissue has progressed in the orthopedic medical arts, there has been a need for medical devices which can be used to attach tendons, ligaments and other soft tissue to bone. When surgically repairing an injured joint, it is preferable to restore the joint by reattaching the damaged soft tissues rather than replacing them with an artificial material. Such restorations typically require the attachment of soft tissue such as ligaments and tendons to bone.

An increase in the incidence of injuries to joints involving soft tissue has been observed. This increased incidence may be due, at least in part, to an increase in participation by the public in various physical activities such as sports and other recreational activities. These types of activities may increase the loads and stress placed upon joints, sometimes resulting in joint injuries with corresponding damage to associated soft tissue. In 1991, for example, there were approximately 560,000 surgical procedures performed in the United States in which soft tissue was attached to a bone in various joints including the shoulder, hip and knee.

One conventional orthopedic procedure for reattaching soft tissue to bone is performed by initially drilling holes or tunnels at predetermined locations through a bone in the vicinity of a joint. Then, the surgeon approximates soft tissue to the surface of the bone using sutures threaded through these holes or tunnels. This method, although effective, is a time consuming procedure resulting in the generation of numerous bone tunnels. The bone tunnels, which are open to various body fluids and infectious agents, may become infected or break. Other known complications may arise including a longer bone-healing period, etc. A known complication of drilling tunnels across bone is that nerves and other soft tissue structures may be injured by the drill bit or orthopaedic pin as it exits the far side of the bone. Also, it may be anatomically impossible or at least very difficult to reach and/or secure a suture/wire that has been passed through a tunnel. When securing the suture or wire on the far side of the bone, nerves and soft tissues can become entrapped and damaged.

Another conventional orthopaedic procedure is that of repairing torn or injured soft tissues such as menisci in the knee. Various kinds of devices have been designed to facilitate insertion of sutures through both sides of the meniscus, but they have been fraught with technical difficulty and some complications such as injury to the blood vessels and nerves. In order to overcome some of the problems associated with the use of the conventional bone tunnel procedures, suture anchors have been developed and are frequently used to attach soft tissue to bone or bone to bone. A suture anchor is an orthopedic, medical device which is typically implanted into a cavity drilled into a bone. These devices are also referred to as bone anchors. In use, the suture anchor is emplaced within the bone and a suture is attached to a portion thereof which is in turn attached to the soft tissue or bone to keep the soft tissue or bone in place against the anchoring bone, for healing purposes. The tension exerted upon the suture, resisted on one end by the emplaced suture anchor, maintains contact between bone and soft tissue. The cavity is typically referred to as a bore hole and usually does not extend through the bone. This type of bore hole is typically referred to as a "blind hole". The bore hole is typically drilled through the outer cortex layer of the bone and into the inner cancellous layer. The suture anchor may be engaged in the bore hole by a variety of mechanisms including friction fit, barbs which are forced into the cancellous layer of bone, etc. Suture anchors are known to have many advantages including reduced bone trauma, simplified application procedures, and decreased likelihood of suture failure. Suture anchors may be used in the Bankart shoulder reconstruction for repairing a lesion of the labrum of the glenoid ligament and may also be used in various orthopedic surgical procedures including those involving rotator cuff repair, ankle, elbow, foot, knee, hand and wrist repair, hip replacement, knee replacement and other bony procedures, such as sternotomy.

Suture anchors typically have a hole or opening for receiving a suture. The suture extends out from the bore hole and is used to attach soft tissue. The suture anchors presently described in the art may be made of absorbable materials that absorb over time, or they may be made from various non-absorbable, biocompatible materials. Although most suture anchors described in the art are made from non-absorbable materials, the use of absorbable suture anchors may result in fewer complications since the suture anchor is absorbed and replaced by bone over time. In addition, the use of absorbable suture anchors may reduce the likelihood of damage to local joints caused by anchor migration. Moreover, when an absorbable suture anchor is fully absorbed it will no longer be present as a foreign body.

Although suture anchors for attaching soft tissue to bone are available for use by the orthopedic surgeon, there is a constant need in this art for novel suture anchors having improved performance characteristics, such as ease of insertion and greater resistance to "pull-out".

DISCLOSURE OF THE INVENTION

Therefore, it is an object of the present invention to provide a suture anchor device that is mechanically stable when implanted in bone and which is simple to apply.

It is a further object of the present invention to provide a suture anchor device that is easy to manufacture.

It is a further object of the present invention to provide an absorbable suture anchor device.

The present invention now provides a suture anchor device, comprising an elongated anchor member having a distal end and a proximal end, a shaft extending proximally away from said anchor member proximal end, and a plurality of wing members extending proximally and radially outward from said anchor member proximal end and terminating in a free end, said wing members being spaced from said shaft; and an operating member comprising a slidable member such as a ring or an elongated sleeve (with either full or partial enclosure) slidably mounted on said shaft for sliding movement relative to said anchor member from a normal position remote from said anchor member to an operative position in which said sleeve is lodged between said shaft and said wing members to thereby restrain said wing members from moving inwardly toward said shaft from the radially outward extending position; and suture retaining means.

Preferably, the sleeve has a wedge-shaped distal portion that tapers inwardly toward the distal end of the sleeve.

The sleeve and the shaft preferably have cooperating locking means for locking the sleeve to the shaft when the sleeve is in the pre-actuated position.

Further, the sleeve and the shaft preferably have cooperating locking means for locking the sleeve to the shaft when the sleeve is in the operative position, whereby the wing members are prevented by the locked sleeve from deflecting inwardly from the radially outward extending position.

In another embodiment, the sleeve is lodged between the shaft and the wing members to thereby further extend and hold the wing members in a radially outward further extending position.

The present invention also provides a method of inserting the suture anchor device into a bone, and a suitable applicator for so doing.

The present invention is illustrated in terms of its preferred embodiments in the accompanying drawings.

BRIEF DESCRIPTION OF THE DRAWINGS

FIG. 16 is a top view of the suture anchor device of FIG. 15 in fully assembled form;

FIG. 17 is a side view of the suture anchor device of FIG. 16;

FIG. 18 is a cross-sectional view along View Line 18—18 of FIG. 16;

BEST MODE FOR CARRYING OUT THE INVENTION

Figure 1:
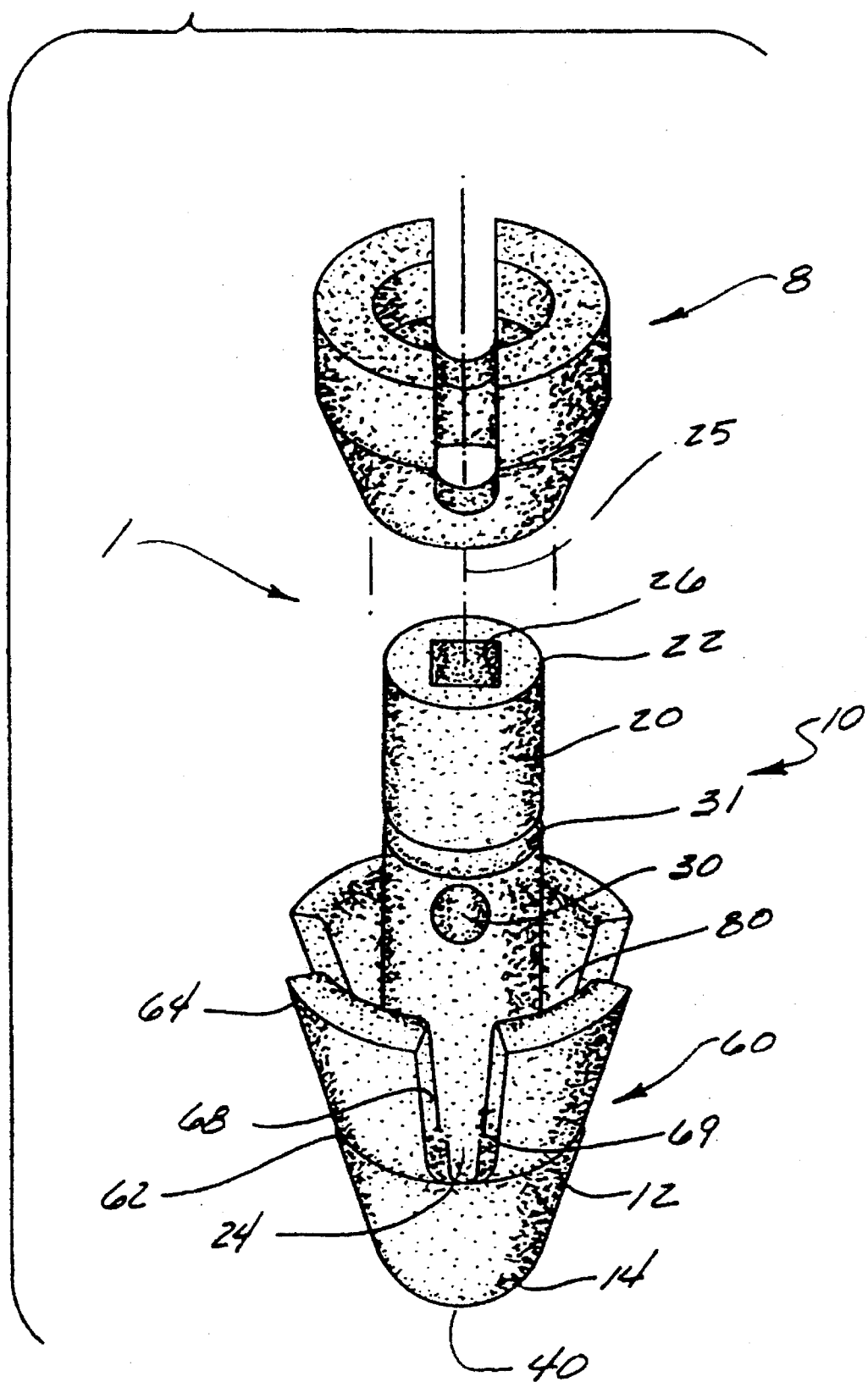
FIG. 1 is a perspective exploded view of a suture anchor device of the present invention comprising an anchor member and an operating member.
Figure 2:
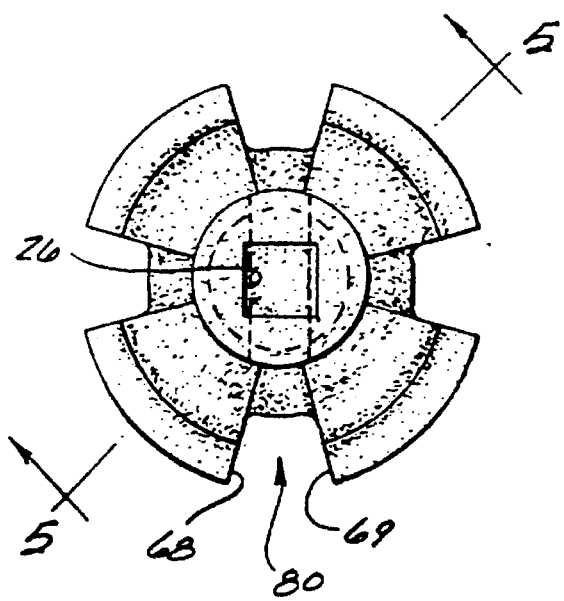
FIG. 2 is a top view of the anchor member of FIG. 1.
Figure 4:
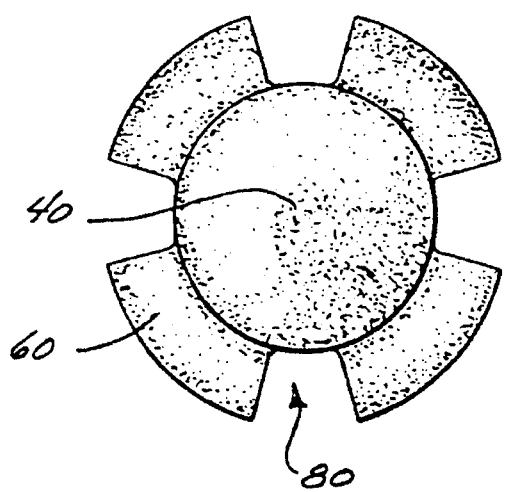
FIG. 4 is a bottom view of the anchor member of FIG. 1.
Figure 3:
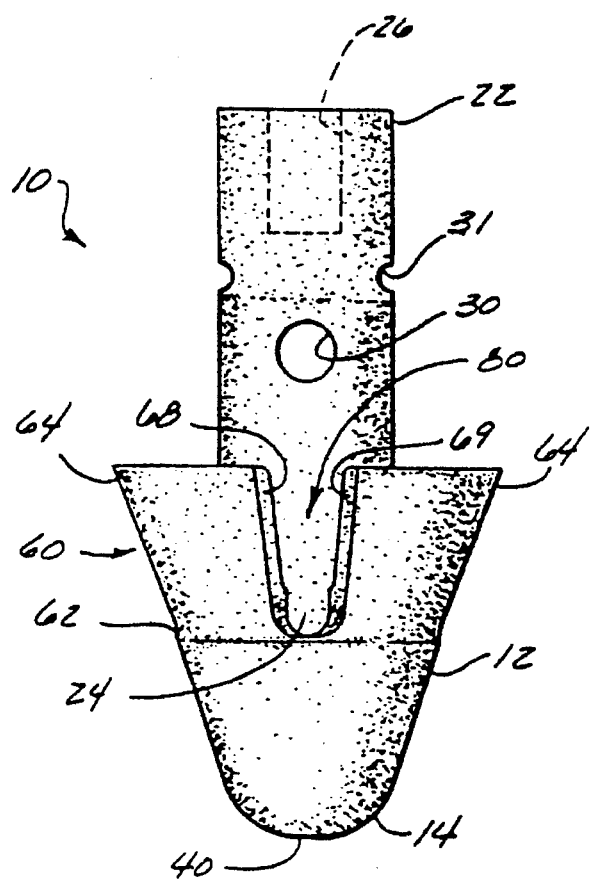
FIG. 3 is a side view of the anchor member of FIG. 1.
Figure 5:
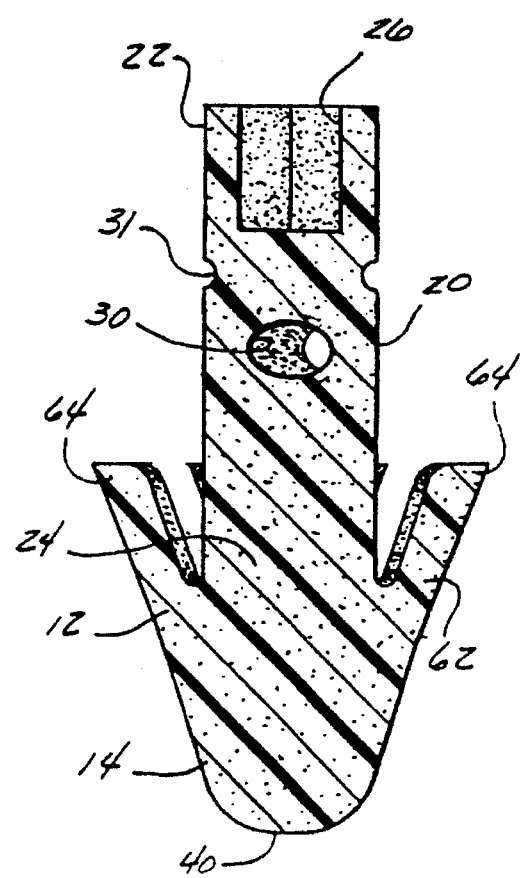
FIG. 5 is a cross-sectional view along View Line 5—5 of the anchor member of FIG. 2.
Figure 6:
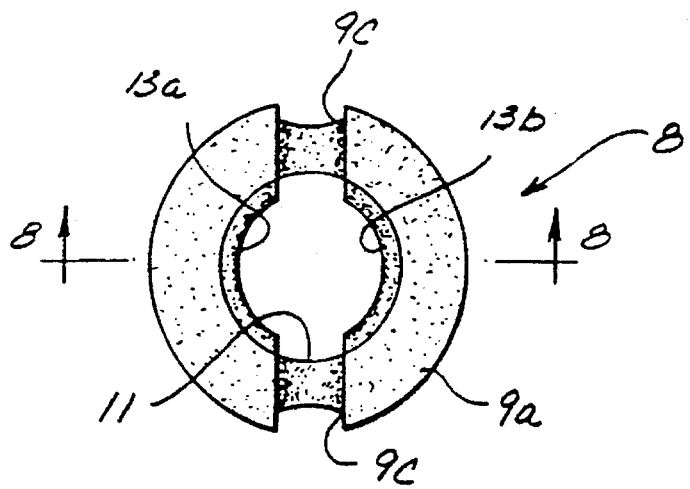
FIG. 6 is a top view of the operating member of FIG. 1.
Figure 7:
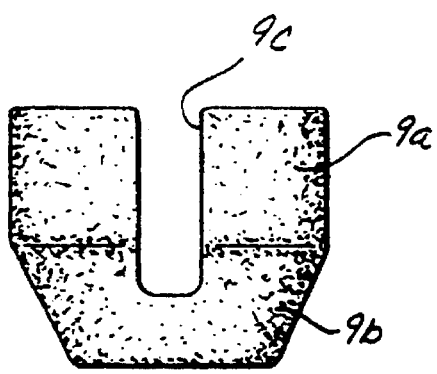
FIG. 7 is a side view of the operating member of FIG. 1.
Figure 8:
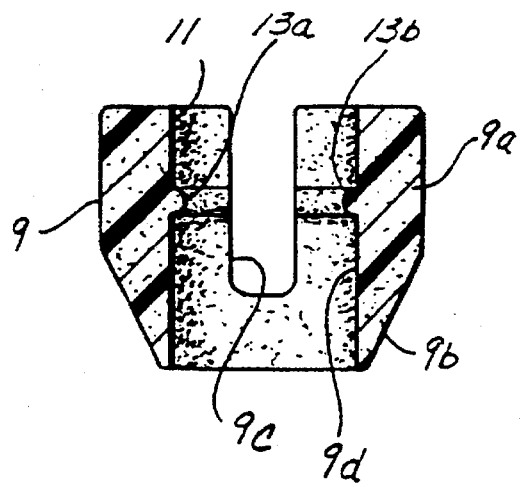
FIG. 8 is a cross-sectional view along View Line 8—8 of FIG. 6.
Figure 9:
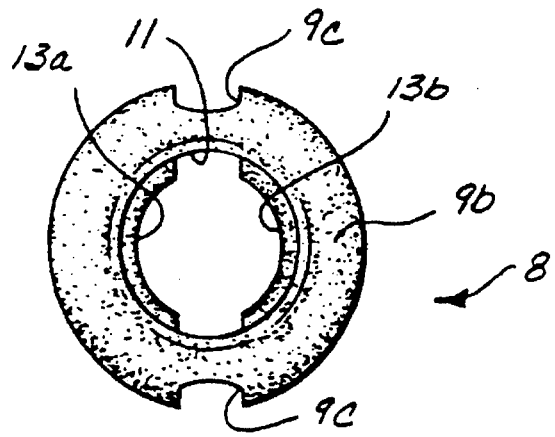
FIG. 9 is a bottom view of the operating member of FIG. 6.
Figure 10:
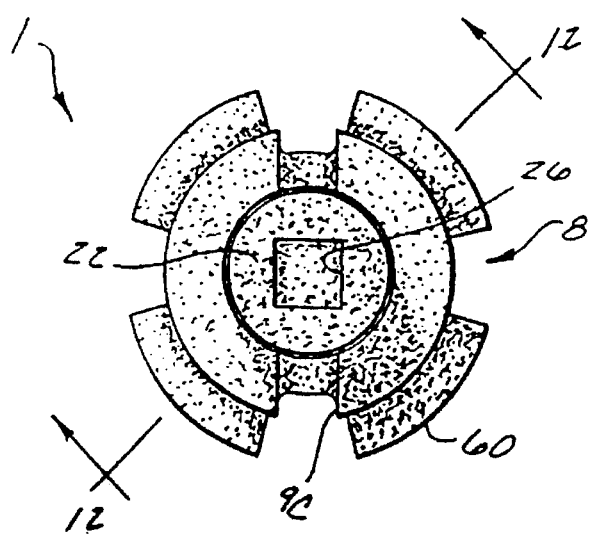
FIG. 10 is a top view of the suture anchor device of the invention in fully assembled form.

The suture anchor device 1 of the present invention is seen in FIGS. 1–12. Referring to FIGS. 1–5, the suture anchor device comprises an operating member 8 and an anchor member 10. Anchor member 10 includes a distal end 14 and proximal end 12. Anchor member 10 preferably has a circular cross-section which may vary in diameter along its longitudinal axis. The anchor member 10 may have other geometric cross-sections including square, rectangular, triangular, polyhedral, elliptical, etc. A central shaft 20 having proximal end 22 and distal end 24 extends from the proximal end 12 of anchor member 10. The shaft 20 is seen to have longitudinal axis 25. The shaft 20 has suture hole 30 extending therethrough transverse to longitudinal axis 25. Suture hole 30 is preferably positioned below retaining groove 31 and is preferably circular in configuration but may have other geometric configurations or other shape such as geometric, blunted, etc. Extending from the distal end 14 of anchor member 10 is blunt distal nose section 40. If desired, distal nose 40 may be tapered or pointed.

Extending from the proximal end 12 of anchor member 10 are the wing members 60. The wing members 60 are spaced from shaft 20 and each extends proximally and radially outward from proximal end 12. Wing members 60 have a fixed distal end 62 and a free proximal end 64 as well as opposed sides 68 and 69. The wing members 60 are separated from each other by slots 80. The wing members may vary in number size and shape from those shown with equal effect.

Referring now to FIGS. 6–9, operating member 8 comprises a slidable member such as a ring or an elongated sleeve 9 having a central bore 11 therethrough. Sleeve 9 comprises a proximal portion 9a of preferably circular cross-section and a preferably inwardly tapering distal portion 9b. Opposed slots 9c are formed in tubular body 9 extending through proximal portion 9a and into distal portion 9b. Slots 9c cooperate with suture hole 30 as will be described hereinafter.

Two substantially semi-circular, opposed ribs 13a, 13b extend from inner surface 9d into bore 11. Ribs 13a, 13b cooperate with preferred, though optional groove 31 of anchor member 10 as will be described hereinafter.

Figure 12:
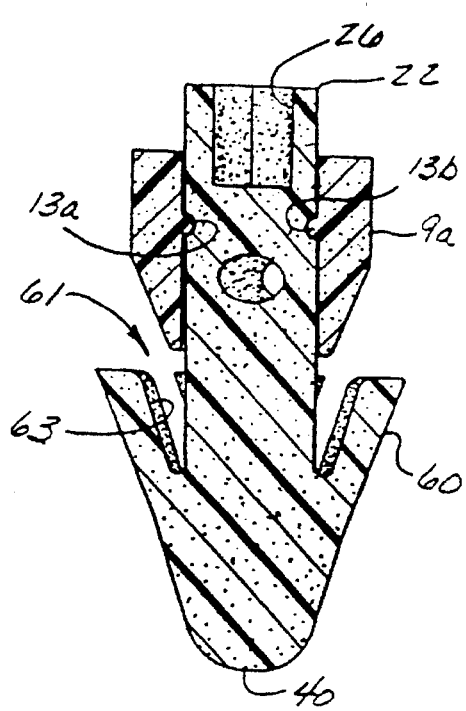
FIG. 12 is a cross-sectional view along View Line 12—12 of FIG. 10.
Figure 11:
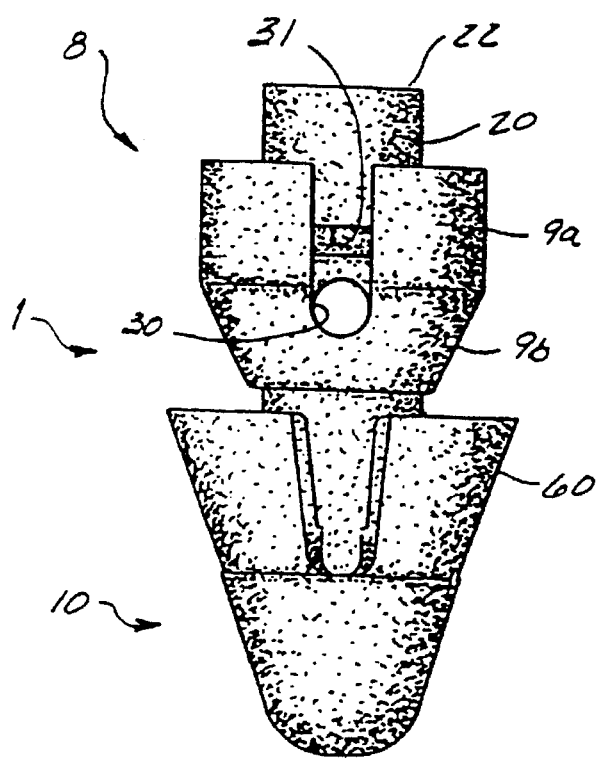
FIG. 11 is a side view of the suture anchor device of FIG. 10.

Referring now to FIGS. 10–12A, the operating member 8 is mounted to the anchor member 10 to form the suture anchor device 1 of the present invention by slidingly inserting shaft 20 into bore 11 of operating member 8 until ribs 13a, 13b snap into groove 31, as best shown in FIG. 12. The sleeve 9 is sufficiently resiliently deformable to allow the ribs 13a, 13b to ride over shaft 20 and to snap into groove 31.

Figure 12A:
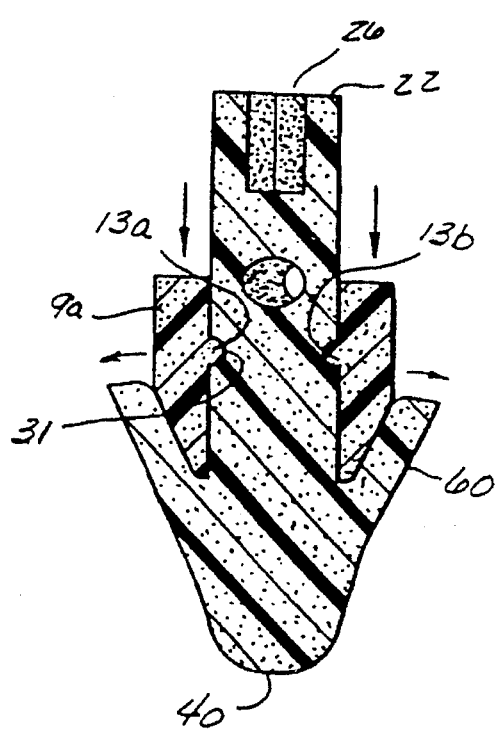
FIG. 12A is a view similar to FIG. 12 showing the operating member locking the wing members in an anchoring position.

As the operating member 8 and anchor member 10 are moved relative to one another as shown by arrows A and/or B, respectively, in FIG. 12, ribs 13a, 13b will be disengaged from groove 31 and the distal portion 9b will enter each passageway 61 (FIG. 12) formed between shaft 20 and the wing 60 adjacent thereto. Continued relative movement between operating member 8 and anchor member 10 will cause the distal portion 9b first to engage the inner surface 63 (FIG. 12) of each wing 60 and then become wedged between wings 60 and shaft 20, thereby locking the wings 60, as shown in FIG. 12A, in an anchoring position. It is preferred that such anchoring position be that of the normal unstressed configuration of the wings 60. In such embodiment, distal portion 9b is sized to fit within passageway 61, without spreading wings 60 beyond the normal resting position. Alternatively, as shown in FIG. 12C, the distal portion 9b is slightly larger than passageway 61, to thereby cause the wings 60 to deflect outwardly from the at rest position. Overextending the deflection of the wings beyond the resting state may result in residual stress which may be less desirable. In either embodiment, slots 9c expose opening 30 when the operating member 8 is in the position shown in FIG. 12A or 12C.

While distal portion 9b is shown as wedge-shaped in the drawings, it may be of any shape, such as cylindrical, so long as the sleeve 9 is capable of spreading the wing members 60 to their further outward position.

Figure 12B:
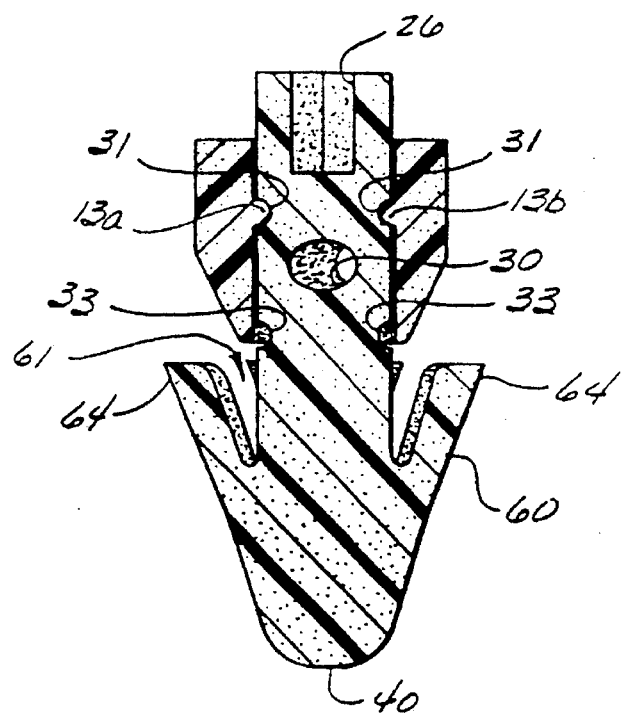
FIGS. 12B and 12C are views similar to FIGS. 12 and 12A, respectively, of another embodiment of the invention.
Figure 12C:
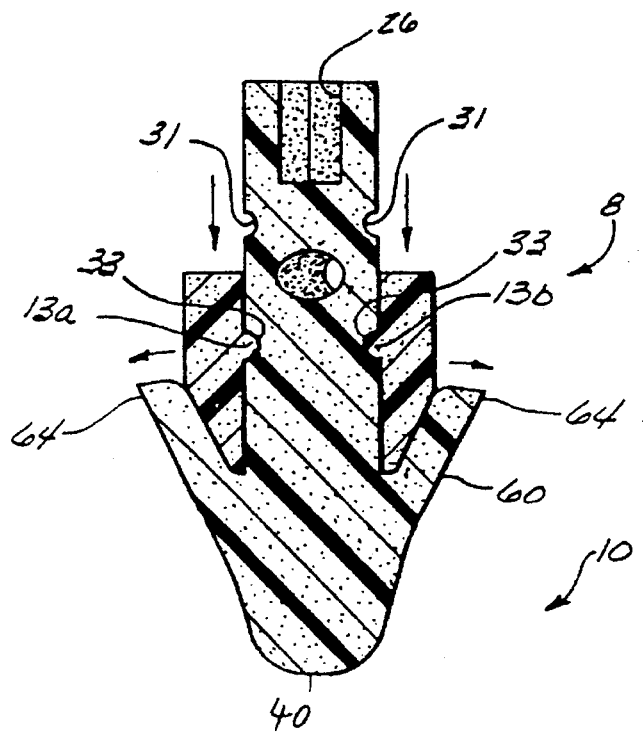

The alternative embodiment of the invention shown in FIGS. 12B and 12C employs a second groove 33 below groove 31, whereby ribs 13a and 13b lock the member 8 to shaft 20 before insertion into a bone, as shown in FIG. 12B, and the ribs 13a and 13b then engage second groove 33, after operating member 8 spreads wing members 60 to the further outward position (FIG. 12C). When the operating member 8 is moved or locked in place in the positions shown in FIG. 12A or 12C, the wing members 60 cannot be deflected inwardly.

Figure 13:
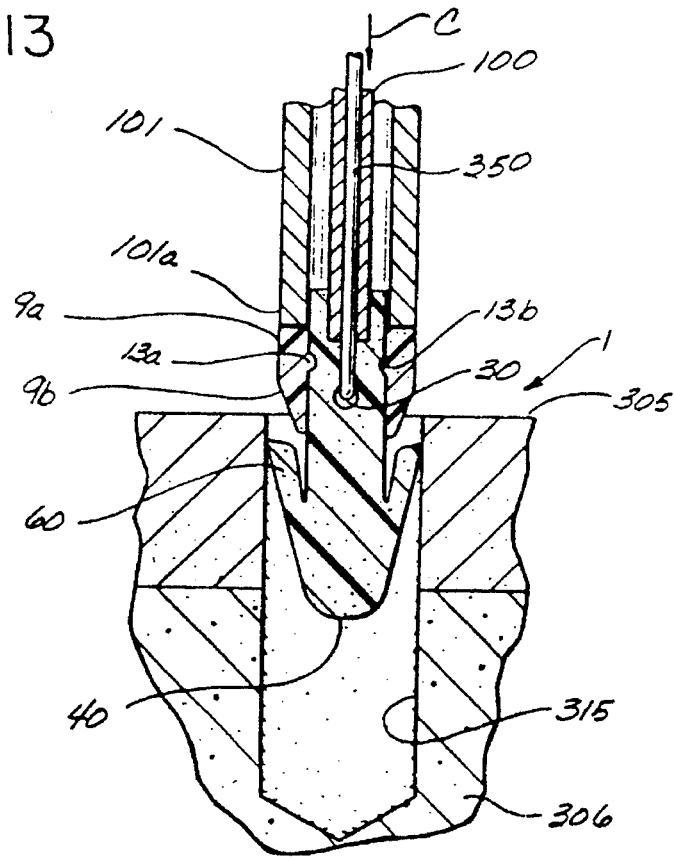
FIG. 13 is a schematic views similar to FIGS. 12 and 12A, respectively, showing the suture anchor device being inserted into a bone.
Figure 14:
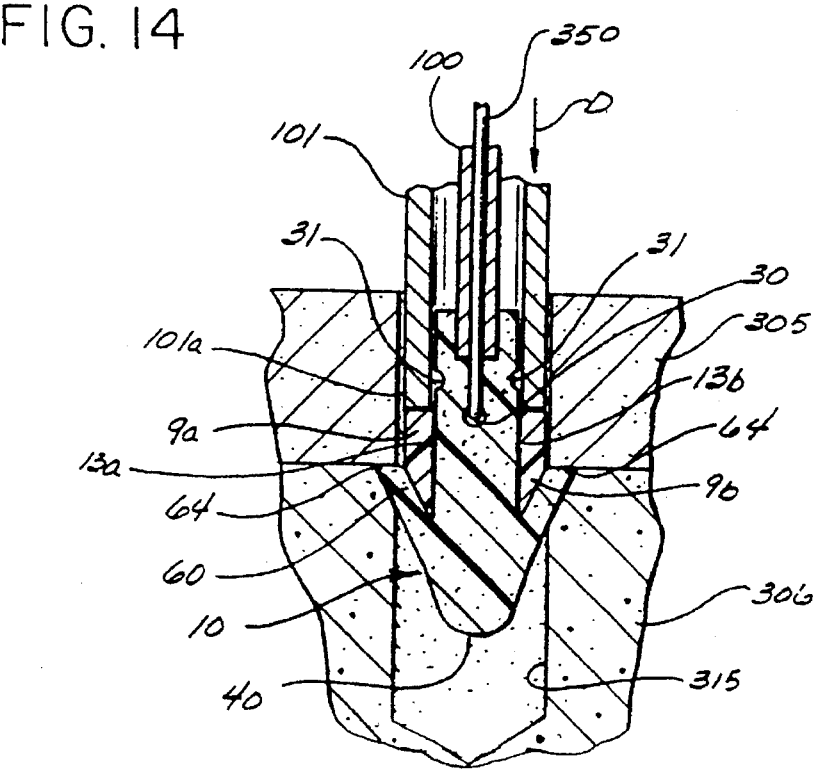
FIGS. 14, 14A and 14B are schematic views similar to FIG. 12 showing the suture anchor device emplaced in bone at various depths of the bone bore hole.
Figure 14A:
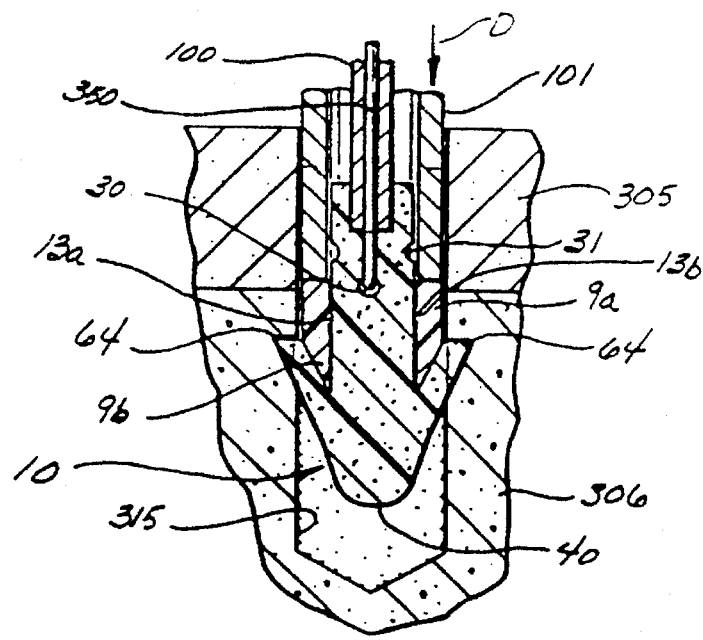
Figure 14B:
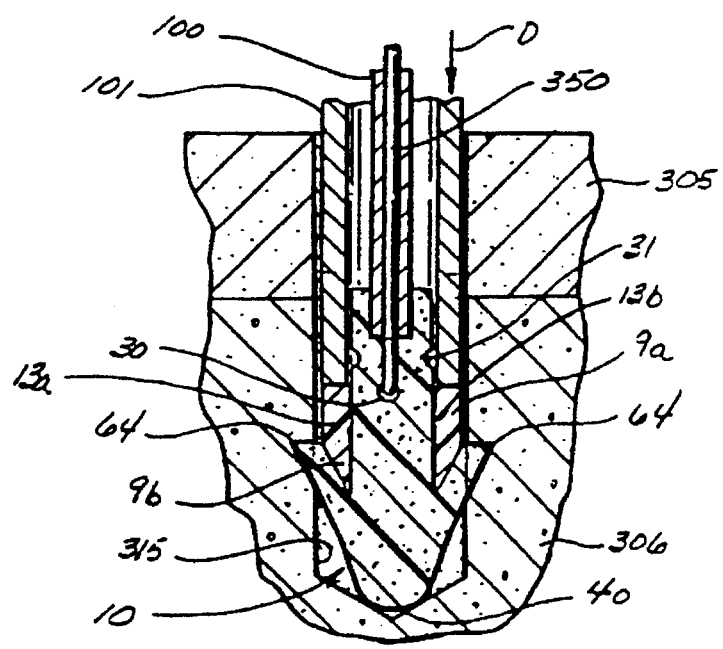
Figure 15:
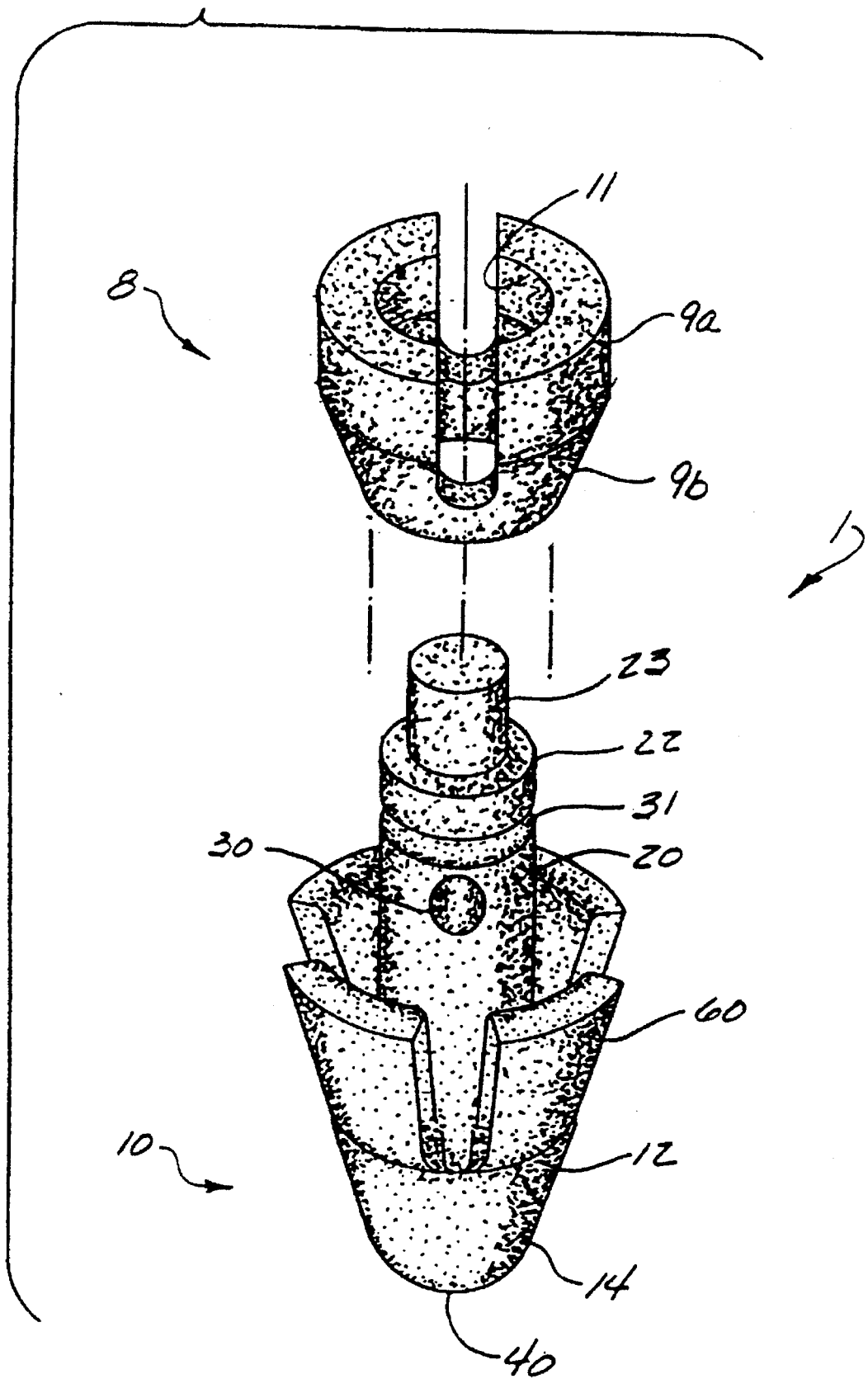
FIG. 15 is a view similar to FIG. 1 of another embodiment of the invention.
Figure 19:
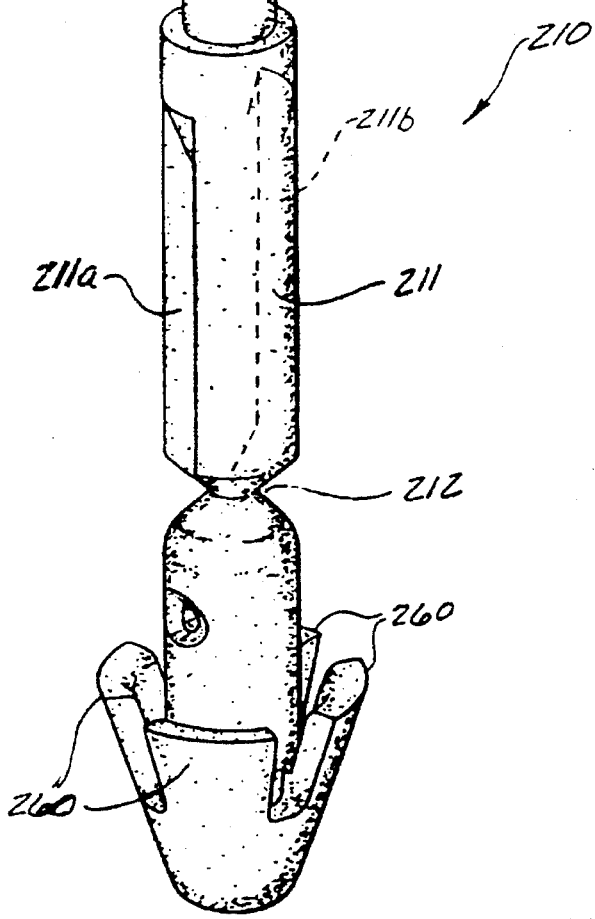
FIG. 19 is a perspective view, similar to that of FIG. 1, showing a further embodiment of the suture anchor of the present invention with a break-away insertion element.
Figure 20:
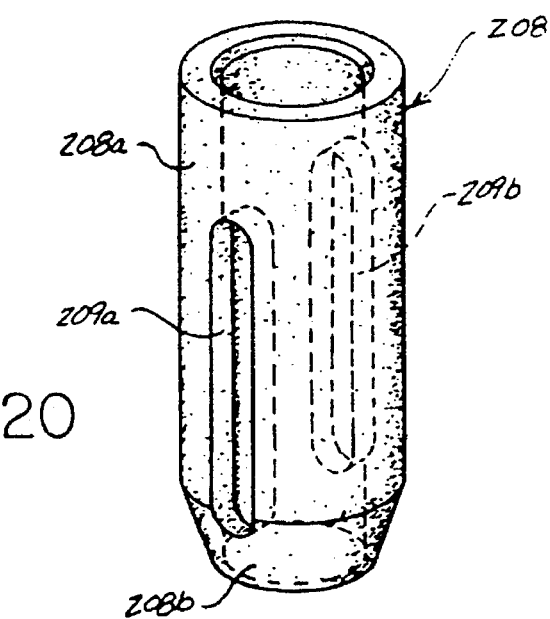
FIG. 20 is a perspective view of the operating member used in conjunction with the suture anchor of FIG. 19.

FIGS. 13 and 14 also illustrate the spreading action of operating member 8. Referring to FIG. 13, a bore hole 315 of sufficient depth is drilled into a bone using conventional surgical drilling instruments. The hole 315 will extend through the outer cortex layer 305 of the bone and into the underlying cancellous layer 306. The suture anchor device 1 is then prepared for insertion into the hole 315 by threading suture 350 through suture hole 30, so that the suture anchor device 1 and a section of suture 350 are inserted as a unit into the hole 315. The diameter of hole 315 drilled into the bone is preferably sized to be less than that of the suture anchor, such that the wing members 60 of the anchor member 10 are compressed and deflected radially inwardly as the suture anchor device is inserted into the hole 315. The wing members 60 are returned to their original position, as shown in FIG. 14, by means of operating member 8. Alternatively, the diameter of hole 315 is equal to or slightly larger than that of the suture anchor, whereby the wing members 60 are not deflected radially inwardly as the suture anchor device 1 is inserted into the hole 315. In such embodiment, operating member 8 spreads the wing members 60 outwardly for anchoring engagement with the bone. Any suitable grasping instrument, such as a pair of conventional surgical tweezers or a suitable surgical grasper can be appropriately utilized for applying or positioning the anchor in place.

FIGS. 13 and 14 illustrate one means of inserting the suture anchor device 1 into the bore hole 315. In particular, a rod 100 having a square cross-section at its distal end is first inserted into the square socket 26 (FIG. 1) of shaft 20, whereby the suture anchor device 1 is securely but releasably held on rod 100. (If socket 26 is of a cross-section other than square, then the distal end of rod 100 will be of a complementary cross-section.) Other means for releasably fastening the suture anchor device to an applicator include press fits, snap-fits (e.g., with a detentable bearing), clamps, etc. Rod 100 is urged in the direction of arrow C in FIG. 13 to move the operating member 8 and anchor member 10 as a unit into bore hole 315. A cannula 101 is slidingly positioned over the rod 100 so that the distal end 101a of cannula 101 engages the top surface of the proximal portion 9a of operating member 8. When the blunt nose 40 is fully inserted or reaches the bottom of bore hole 315, cannula 101 is urged in the direction of arrow D in FIG. 14 to move operating member 8 relative to anchor member 10 such that the ribs 13a, 13b move out of groove 31 and the distal portion 9b moves into spreading engagement with the inner surfaces of wings 60 to force the wings 60 further outwardly and away from the shaft 20. This spreading action will cause the free ends 64 of wings 60 to engage the cancellous bone 306 (the wings may also engage cortical bone or a combination of the cancellous and cortical bone) as the ends 64 move outwardly. Since the free ends 64 are engaged with the cancellous bone, 306, the anchor member 10 is firmly secured in place. The free ends 64 are spaced apart in the FIG. 14 position by a distance greater than the diameter of the bore hole 315, thereby further preventing the suture anchor device 1 from being pulled out of the bone.

It is noted that the diameter of the bore hole 315 is preferably smaller than the largest outside diameter of the suture anchor device 1 whereby the wing members 60 are in unstressed position during anchoring (FIG. 12). Alternatively, the diameter of the bore hole 315 (as described above) is the same as or slightly larger than the largest outside diameter of the suture anchor device 1, when it is desired that the force required to insert the suture anchor device 1 be minimal and the suture anchor device 1 will not be damaged during insertion. After the operating member 8 is engaged, suture anchor device 1 is locked into place in the bone by means of the wing members 60 being in their original extended position or slightly overextended position, which increases the pull-out force required to dislodge device 1. Further, the operating member 8 may act as a centering device.

Once the suture anchor device 1 is locked into place in the bone, the suture 350 is used in a conventional manner to secure a tendon or ligament to bone.

FIG. 15–18 illustrate another embodiment of the invention, in which shaft 20 is provided at its proximal end 22 with an extension 23 rather than the socket 26 shown in FIG. 1. As shown in FIG. 18, a wedge clamp 102 shown in phantom line may be used to insert the suture anchor device 1 of FIG. 18 into a bore hole, the clamp 102 engages extension 23, while cannula 101 may be used to move operating member 8 into spreading engagement with wing members 60 to force the wing members 60 away from rod 20, in the manner described above.

FIG. 19–22 depict a preferred embodiment structure of the suture anchor of the present invention. In this embodiment, suture anchor member 210 embodies an integral break away shaft 211 which aids in proper positioning and which breaks away at narrow section 212 for removal thereof. The shaft 211 embodies integral recesses 211a and 211b to accommodate suture 350 out of the way of the operative emplacement of the anchor in bone. Operating member 208 is similar in function to that of the operating member 8 as described with the previously described embodiments and is comprised of a cylinder 208*a* with a tapered section 208*b*. Closed slots 209*a* and 209*b* accommodate and respectively hold both ends of the suture 350 (as more clearly seen in FIG. 21 and 22) in the longitudinal direction even after shaft 211 has been broken and removed. Proximal ears 214*a* and 214*b* on shaft 211 are adapted for ready engagement with an applier (not shown). In operation, the operating member 208 and anchor member 210 are moved relative to each other. The operating member 208 may be restrained while the anchor member 210 is moved. They may be moved in opposite directions relative to each other, or the operating member 208 may be moved while the anchor member 210 remains stationary.

Figure 22:
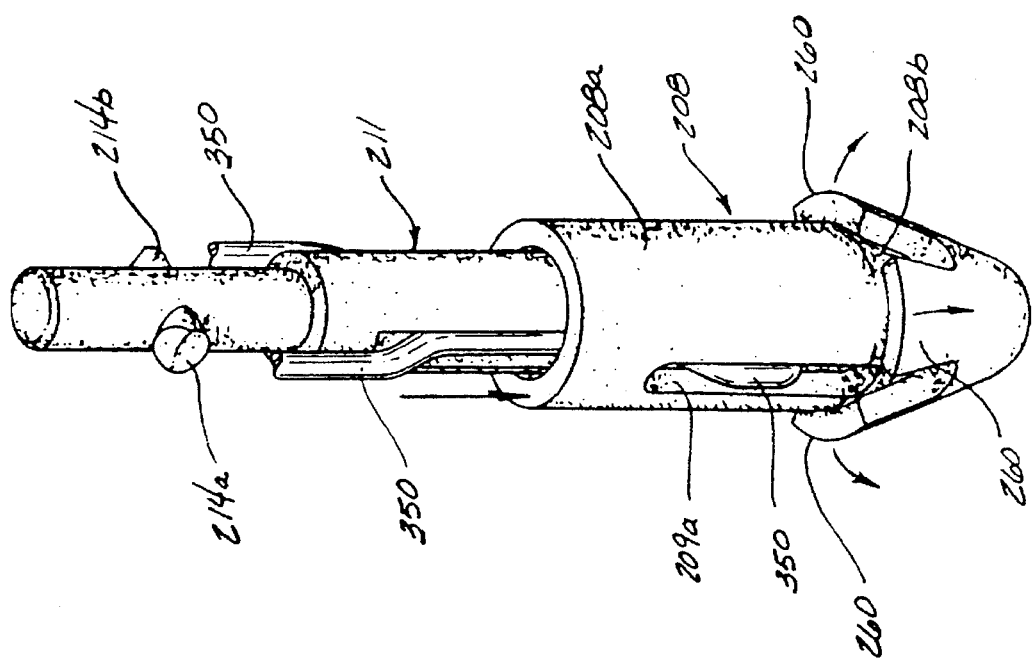
FIG. 22 is a perspective view of the assembled suture anchor of FIG. 21 after activation.
Figure 21:
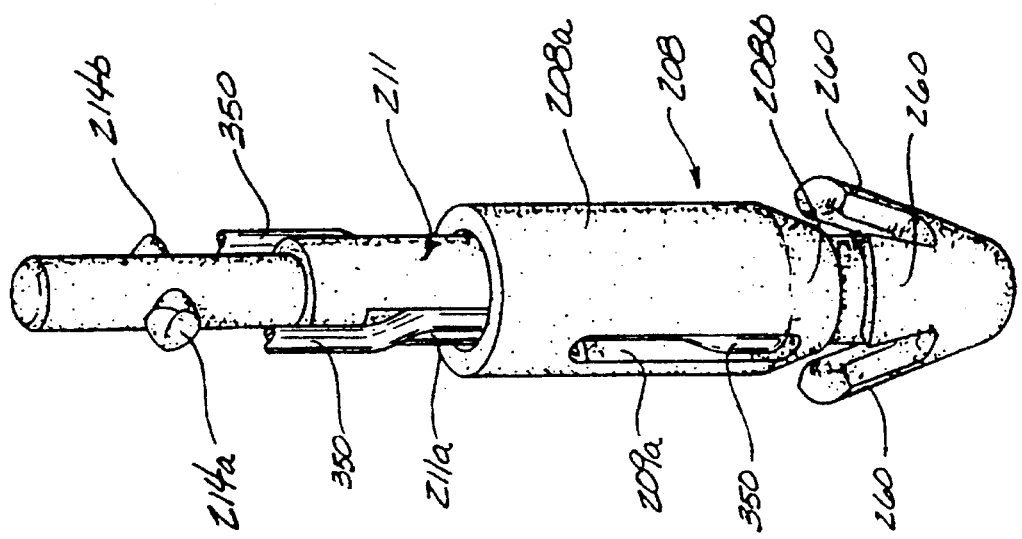
FIG. 21 is a perspective view of the suture anchor of FIG. 19 and the operating member of FIG. 20 assembled with suture therein, prior to activation.

As shown in FIG. 21 and 22, tapered section 208*b* is pressed into the head of suture anchor 210 into wedged engagement with wings 260, to maintain them in position for anchoring, such as described above with the previous embodiments.

The operating member and anchor member of the present invention may be made from either conventional bioabsorbable materials or conventional non-absorbable materials, combinations thereof and equivalents thereof. Examples of absorbable materials include homopolymers and copolymers of lactide, glycolide, trimethylene carbonate, caprolactone, and p-dioxanone and blends or other combinations thereof and equivalent thereof. Of particular utility are the polylactides, especially poly[L(-)lactide], and the lactide-rich lactide/glycolide copolymers, especially 95/5 poly[L(-)lactide-co-glycolide].

Other types of absorbable materials include the calcium-phosphate ceramics, such as hydroxyapatite (HA), which may be sintered into three-dimensional geometries, or calcium-phosphate based glasses, which may be molded into solid forms. An additional advantage of this approach would be the osteogenic potential of the implant during absorption, due to the similarity in composition of the calcium-phosphate materials to the mineral constituent of cortical bone. In addition, the invention may be comprised of absorbable composites of the listed absorbable polymers and absorbable ceramics, which would offer the advantages of superior mechanical properties (higher strength and modulus) relative to the non-filled polymer, in addition to the osteogenic potential. Examples of such composites are described by Steckel in: "Physio-Mechanical Properties of Absorbable Composites: CSM Short Fiber Reinforced PDS and PGA" (Ph.D. Thesis, Drexel University, 1992).

Examples of non-absorbable materials from which the suture anchors of the present invention may be made include metallic biocompatible materials including stainless steel, Nitinol, titanium, Ti-6Al-4V and its related alloys, Co—Cr alloys, Vitalium, and equivalents thereof, polymeric materials such as non-absorbable polyesters, polyamides, polyolefins, polyurethanes, and polyacetals and equivalents thereof, and ceramic materials such as alumina and equivalents thereof.

The suture anchor devices of the present invention, when made from an absorbable material, are preferably manufactured by molding using conventional injection molding equipment and conventional injection molding processes. A typical molding process includes the steps of (1) injecting a suitable polymer melt into an appropriately designed mold or cavity at process conditions conventionally employed for such polymer systems, (2) releasing from the mold, after the melt cools in the mold, polymer shaped in the proper configuration to meet the design criteria of the device. Additionally the anchor molded from the absorbable polymeric material, may be advantageously subjected to an annealing process to increase its mechanical or biological performance. Thermal annealing can also be used to increase the dimensional stability of molded parts by increasing the crystallinity levels in the parts. One or more surgical sutures, or one or more sutures with surgical needles attached, may be used in combination with the suture anchor and may be assembled prior to sterilization. The device can then be sterilized using conventional methods to render the anchor suitable for surgical applications.

The bonding of the anchors of the present invention to bone may be advantageously increased by promoting bone growth. This can be accomplished by having a microporous surface into which the bone can rapidly grow to aid fixation. This may be particularly advantageous in the case of a metallic anchor, especially a titanium or titanium alloy anchor, but may also provide benefit in the case of polymeric anchors of the present invention, especially those made of absorbable materials. Other methods include the coating of the anchor's surface with a substance to promote adhesion to the bone. Examples of such coatings include calcium-phosphate based materials, either crystalline or glassy, adhered to the surface of the anchor. One such approach is the plasma spraying of hydroxyapatite to the anchor surface, although other techniques are available such as electrophorotic deposition, sputtering, or sol-gel deposition. Such coatings include the hydroxyapatite-containing-glass coatings described by Ishikawa, et al., in the article "Effect of Hydroxyapatite Containing Glass Coatings on the Bonding between Bone and Titanium Implants" appearing in Clinical Materials, Volume 14, (1993) pages 277–285, the teachings of which are incorporated herein by reference thereto.

It is further noted that the anchors of the present invention can be made to contain growth factors, especially bone growth factors, that can advantageously increase the effectiveness of the anchors, especially in the area of fixation. This may be accomplished in a number of ways, including via coatings or, in the case of absorbable materials, by incorporating the growth factors within the device and allowing them to diffuse out.

The surgical needles 360 and sutures 350 which may be used with the suture anchor device of the present invention include conventional sutures and conventional surgical needles and equivalents thereof. The sutures 350 may be absorbable or non-absorbable. The non-absorbable sutures 350 may be made from conventional materials including polyester, nylon, polypropylene, stainless steel, Vitalium alloy, Nitinol and the like and combinations thereof and equivalents thereof. The absorbable sutures 350 may be made from conventional materials such as poly(p-dioxanone), 95/5 poly[L(-)lactide-co-glycolide] or combinations thereof and equivalents thereof.

The surgical needles 360 which may be used include conventional surgical needles such as stainless steel needles having conventional straight or curved configurations with conventional points such as taper points or cutting points or blunt points.

The suture anchor device of the present invention has numerous advantages. The suture anchor device of the present invention is very easy to manufacture. The suture anchor device has stability when emplaced in bone and is easy to use. The suture anchor device of the present invention does not simply rely on the friction between the device and the side walls of a hole drilled through bone to maintain its position within a bone, rather, it utilizes a mechanical lock between the proximal edges of the wing members and the bone surrounding the bore hole.

The suture anchor device of the present invention can be used to reattach soft tissues to bone and other soft tissues at various anatomical locations including the shoulder joint, elbow, wrist, hand, ankle, hip joint, knee joint, etc., in either open or arthroscopic or endoscopic surgical procedures. The suture anchor device, preferably when of a larger size, may also be used for fixation of bone fractures, or attachment of soft tissue to soft tissue, or even attachment of medical devices to bone, or soft tissue.

The suture anchor device of the present invention may be used in a variety of surgical techniques including open procedures, arthroscopic procedures, laparoscopic procedures and endoscopic procedures, including closure of sternotomy incisions.

EXAMPLE 1

A patient is prepared for surgery using conventional surgical preparatory techniques. The patient is anesthetized with a sufficient dose of a conventional anesthesia to induce an effective anesthetized state. An incision is made into the patient's knee joint in accordance with conventional surgical procedures and the end of the patient's femur adjacent to the knee joint is exposed. A bone hole is bored into the patient's femur using a conventional boring instrument such as an orthopaedic drill. After a blind hole has been bored into the patient's femur and the bone surface has been cleaned of tissue debris, a surgical anchor device of the present invention having a suture and surgical needle is inserted into the bore hole using an applicator such that the proximal end of the central shaft (or break-off position of the shaft) and suture hole are positioned below the outer surface of the cortex of the bone surrounding the bore hole. The proximal ends of the wing member are positioned below the innermost surface of the cortex and are within the cancellous layer. The diameter of the bore hole is selected so that the wing members of the anchor are deflected sufficiently radially inward during insertion to effectively prevent the anchor from moving within the bore hole. The deflection is a substantially elastic deformation. The operating member is then deployed to effectively cause the wings to open to their original diameter, with further prevention of inward deflection. The cutting edges on the sides of each wing cut into the cancellous layer thereby enlarging the diameter of the bore hole in the proximity of the wing member to allow the wing member to move radially outwardly to its original position. The anchor is released from the grasping apparatus. The wing members now have a maximum outside diameter greater than the diameter of the bore hole, but equal to their original undeformed diameter. Therefore, a proximal force exerted upon the bone anchor is resisted by the wing member digging into the cancellous layer and preferably engaging the inner surface of the cortex thereby preventing the anchor from being withdrawn from the bore hole. A tendon or ligament is then secured to the anchor using the surgical needle and suture. The incision in the patient's knee is then closed in accordance with conventional surgical procedures.

EXAMPLE 2

A patient is prepared for arthroscopic shoulder surgery using conventional surgical preparatory techniques. The patient is anesthetized with a sufficient dose of a conventional anesthesia to induce an effective anesthetized state. Arthroscopic trocar cannulas are placed into the patient's shoulder in accordance with conventional arthroscopic techniques. An arthroscope is inserted through one cannula and upon examination, a soft tissue lesion is identified. An appropriately sized hole is drilled into the patient's scapula, in the area of the glenoid rim, using a conventional boring instrument such as a drill bit or orthopaedic pin inserted through a trocar cannula. After the patient's scapula and the bone surface have been cleaned of tissue debris, a surgical anchor device of the present invention having a suture and surgical needle is inserted through a trocar cannula and into the bore hole using an applicator (the distal end of which is inserted into the trocar cannula) such that the proximal end of the central shaft (or break-off position of the shaft) and suture hole are positioned below the outer surface of the cortex of the bone surrounding the bore hole. The proximal ends of the wing member are positioned below the innermost surface of the cortex and are within the cancellous layer. The diameter of the bore hole is selected so that the wing members of the anchor are deflected sufficiently radially inward during insertion to effectively prevent the anchor from moving within the bore hole. The deflection is a substantially elastic deformation. The operating member is then deployed to effectively cause the wings to open to their original diameter, with further prevention of inward deflection. The cutting edges on the sides of each wing cut into the cancellous layer thereby enlarging the diameter of the bore hole in the proximity of the wing member to allow the wing member to move radially outwardly to its original position. The anchor is released from the grasping apparatus through the trocar cannula. The wing members now have a maximum outside diameter greater than the diameter of the bore hole. Therefore, a proximal force exerted upon the bone anchor is resisted by the wing member digging into the cancellous layer and preferably engaging the inner surface of the cortex thereby preventing the anchor from being withdrawn from the bore hole. A tendon or ligament is then secured to the anchor using the surgical needle and suture. The arthroscopic trocar cannulas are removed and the incisions in the patient's shoulder are then closed in accordance with conventional arthroscopic surgical procedures.

EXAMPLE 3

A standard arthroscopy of the knee is carried out under sterile conditions. A repairable meniscal "red-red" tear is found and identified. The edges of the tear are prepared in the appropriate manner to enhance healing. A modified drill guide of the present invention is then taken. This drill guide encompasses two sharp points which can puncture the proximal edge of the meniscal tear to hold it in place. At this point a small drill or wire is used to perforate both proximal and distal edges of the meniscal tissue. A stop is placed on the drill to prevent deep penetration.

The drill is removed with the drill guide left in place so that the bore hole is not lost. A suture anchor of this embodiment is inserted through the guide to come out behind the peripheral rim. The anchor is then set and the suture is pulled through the standard arthroscopic wound. At this point the appropriate number of anchors are inserted, consistent with how many sutures are needed. Typically this would be two or three sutures requiring three to six anchors, depending on whether or not one or two sutures are available on each anchor.

The appropriate sutures are then tied to each other using standard arthroscopic technique with the use of knot tying and knot pushing equipment.

The suture anchors of the present invention may be used in a variety of surgical techniques including open procedures, arthroscopic procedures, laparoscopic procedures and endoscopic procedures. Although this invention has been shown and described with respect to detailed embodiments thereof, it will be understood by those skilled in the art that various changes in form and detail thereof may be made without departing from the spirit and scope of the claimed invention.

What is claimed is:

1. A suture anchor assembly, comprising
   an elongated anchor member having
      a distal end and a proximal end,
      a shaft extending proximally away from said anchor member proximal end, and
      a plurality of wing members extending proximally and radially outward from said anchor member proximal end and terminating in a free end, said wing members being spaced from said shaft;
   an operating member slidably mounted on said shaft for sliding movement relative to said anchor member from a first normal position remote from said anchor member to an operative position in which said operating member is lodged between said shaft and said wing members to thereby restrain said wing members from moving inwardly toward said shaft from the radially outward extending position; and
   suture retaining means in said shaft.

2. The assembly of claim 1, wherein said operating member is a sleeve.

3. The assembly according to claim 2, wherein said sleeve has opposed proximal and distal ends, said sleeve having a wedge-shaped distal portion that tapers inwardly toward said sleeve distal end.

4. The assembly according to claim 3, wherein said suture retaining means comprises two slots in said cylinder, with each slot extending from the distal to proximal ends of said operating member, and wherein each of said slots overlies an aperture in said shaft, through which the suture is adapted to extend.

5. The assembly according to claim 2, wherein said sleeve and said shaft have cooperating locking means for locking said sleeve to said shaft when said sleeve is in said normal position.

6. The assembly according to claim 5, wherein said sleeve and said shaft have cooperating locking means for locking said sleeve to said shaft when said sleeve is in said operative position, whereby said wing members are prevented by said locked sleeve from deflecting inwardly from said outward position.

7. The assembly according to claim 2, wherein said sleeve and said shaft have cooperating locking means for locking said sleeve to said shaft when said sleeve is in said operative position, whereby said wing members are prevented by said locked sleeve from deflecting inwardly from said outward position.

8. The assembly according to claim 2, wherein said anchor member and said sleeve each comprises a bioabsorbable material.

9. The assembly according to claim 8, wherein the bioabsorbable material comprises a member selected from the group consisting of homopolymers and copolymers of lactide, glycolide, trimethylene carbonate, caprolactone, and p-dioxanone and blends thereof.

10. The assembly according to claim 2, wherein said anchor member and said sleeve each comprises a biocompatible nonabsorbable material.

11. The assembly according to claim 10, wherein the nonabsorbable material comprises a member selected from the group consisting of polyesters, polyamides, polyolefins, polyurethanes, and polyacetals.

12. The assembly according to claim 2, wherein said sleeve is lodged between said shaft and said wing members to thereby further extend and hold said wing members in a radially outward further extending position.

13. The assembly according to claim 1, wherein said anchor member is adapted for anchoring in a bone and wherein said anchor member comprises means to promote bone growth, whereby bonding of the anchor member to the bone is increased thereby.

14. The assembly according to claim 13, wherein said means to promote bone growth comprises a microporous surface of said anchor member which is in contact with said bone.

15. The assembly according to claim 14, wherein said anchor member is comprised of titanium or titanium alloy.

16. The assembly according to claim 13, wherein the anchor member comprises bone growth factors.

17. The assembly according to claim 1, wherein said shaft terminates in a proximal end remote from said anchor member, said shaft proximal end having a socket therein for receiving a rod.

18. The assembly according to claim 1, further comprising a surgical suture mounted in the suture retaining means.

19. The assembly according to claim 1, wherein said suture retaining means is adjacent to the proximal end of said shaft.

20. The assembly according to claim 19, wherein said suture retaining means comprises a hole through said shaft.

21. The assembly according to claim 1, wherein said shaft comprises a proximally extending breakaway portion thereof, wherein said breakaway portion is adapted to facilitate placement of said device in a bone or soft tissue and, after such placement, is adapted to be broken from the shaft and removed.

22. The assembly according to claim 1, wherein said shaft terminates in a proximal end remote from said anchor member, said shaft proximal end being adapted for engagement with a removable clamping member.

23. The assembly according to claim 1, wherein the anchor member is adapted for anchoring in a bone and wherein a surface of the anchor member, in contact with the bone, is coated with a substance to promote adhesion thereof to the bone.

24. The assembly according to claim 1, wherein said operating member is a ring.

25. The assembly according to claim 1, wherein the anchor member comprises means for anchoring in soft tissue for repair of soft tissue.

26. A method of implanting a suture anchor assembly in a bone, comprising:
   I) inserting a suture anchor assembly in a bore hole drilled in a bone, wherein the suture anchor assembly comprises an elongated anchor member having a distal end and a proximal end, a shaft extending proximally away from said anchor member proximal end, and a plurality of wing members extending proximally and radially outward from said anchor member proximal end and terminating in a free end, said wing members being spaced from said shaft; an operating member slidably mounted on said shaft for sliding movement relative to said anchor member from a first normal position remote from said anchor member to an operative position in which said operating member is lodged between said shaft and said wing members to thereby restrain said wing members from moving inwardly toward said shaft from the radially outward extending position; and suture retaining means in said shaft, and II) sliding said operating member of said suture anchor assembly relative to said anchor member thereof from said first position to said operative position.

* * * * *